United States Patent
Zhai et al.

(10) Patent No.: US 8,877,988 B2
(45) Date of Patent: Nov. 4, 2014

(54) SYNTHESIS OF 1-BROMO-3,3,3-TRIFLUOROPROPENE

(71) Applicant: Honeywell International Inc., Morristown, NJ (US)

(72) Inventors: Yian Zhai, Amherst, NY (US); Andrew J. Poss, Kenmore, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/099,649

(22) Filed: Dec. 6, 2013

(65) Prior Publication Data

US 2014/0179960 A1      Jun. 26, 2014

Related U.S. Application Data

(60) Provisional application No. 61/745,195, filed on Dec. 21, 2012.

(51) Int. Cl.
  *C07C 17/00* (2006.01)
  *C07C 17/02* (2006.01)
  *C07C 17/087* (2006.01)

(52) U.S. Cl.
  CPC .................................. *C07C 17/087* (2013.01)
  USPC ......................................... 570/156; 570/154

(58) Field of Classification Search
  USPC .................................................. 570/154, 156
  See application file for complete search history.

(56) References Cited

U.S. PATENT DOCUMENTS 8,198,491 B2    6/2012  Masatoshi

FOREIGN PATENT DOCUMENTS

| CN | 101186556 | A | 5/2008 |
|----|-----------|---|--------|
| CN | 101417166 | B | 5/2011 |
| CN | 102179019 | A | 9/2011 |
| CN | 102206134 | A | 10/2011 |
| CN | 102319498 | A | 1/2012 |
| GB | 772484 | | 4/1957 |
| JP | 2001322955 | A2 | 11/2001 |
| WO | 2005-014512 | A2 | 2/2005 |
| WO | 2012-112827 | A2 | 8/2012 |
| WO | WO 2012/113778 | A1 * | 8/2012 |

OTHER PUBLICATIONS

NI Xiao-min et al., "Experimental Study on Performance of Bromotrifluoropropene/Zeolite 13X Composite Powders in Suppressing Gasoline Fires," China Safety Science Journal, 2011, vol. 21, No. 5, pp. 53-58.
Y.F. Zhang et al. "Fire-extinguishing effectiveness of 1-bromo-3,3,3-trifluoropropene/inert gaseous mixture evaluated by cup burner method," Process Safety and Environmental Protection, 2007, vol. 85, No. 2, pp. 147-152.
Zhou Biao et al., "BTP-N2 extinguishing composite gas ratio optimization and Critical Conditions" Fire Safety Science, 2010, vol. 19, No. 2, pp. 60-67.
R.N. Haszeldine, "Reactions of Fluorocarbon Radicals. Part V. Alternative syntheses for trifluoromethylacetylene (3:3:3-trifluoropropyne), and the influence of polyfluoro-groups on adjacent hydrogen and halogen atoms," Journal of the Chemical Society, 1951, pp. 2495-2504.
R.N. Haszeldine, "Reactions of Fluorocarbon Radicals. Part VII. Addition to trifluoromethyl-substituted acetylenes," Journal of the Chemical Society, 1952, pp. 3490-3498.
A.L. Henne et al., "Trifluoropropyne. II. The Triple Bond and the Acetylenic Hydrogen," Journal of the American Chemical Society, 1952, vol. 74, No. 3, pp. 650-652.
T. Hanamoto et al., "Generation and reactions of trifluoromethylethenyl titanium(II) species," Journal of Organic Chemistry, 2009, vol. 74, No. 19, pp. 7559-7561.
Alan R. Katritzky et al., "2-bromo-3,3,3-trifluoropropene: A facile trifluoromethylacetylene anion synthon," Journal of Fluorine Chemistry, 1996, vol. 80, No. 2, pp. 145-147.
PCT Search Report—PCT/US2013/074075—Mar. 14, 2014.

* cited by examiner

*Primary Examiner* — Jafar Parsa
(74) *Attorney, Agent, or Firm* — Erika S. Wilson

(57) ABSTRACT

In accordance with the present invention, processes for producing bromofluoropropenes in commercial quantities by reacting 3,3,3-trifluoropropyne with hydrogen bromide at elevated temperatures are provided.

15 Claims, No Drawings

US 8,877,988 B2

SYNTHESIS OF 1-BROMO-3,3,3-TRIFLUOROPROPENE

CROSS REFERENCE TO RELATED APPLICATION

The present application claims the benefit of U.S. Provisional Patent Application No. 61/745,195, filed on Dec. 21, 2012, the disclosure of which is incorporated herein by reference in its entirety.

FIELD OF THE INVENTION

The present invention is related to cost effective synthesis of 1-bromo-3,3,3-trifluoropropene. More specifically, the present invention is related to the synthesis of 1-bromo-3,3,3-trifluoropropene from the reaction of 3,3,3-trifluoropropyne and HBr.

BACKGROUND OF THE INVENTION

Chlorofluorocarbons (CFCs) are known and widely used in the industry as solvents, blowing agents, heat transfer fluid, aerosol propellants and other uses. But CFCs are also well-known to have ozone depletion potential (ODP) and are regulated by the Montreal Protocol. A suitable replacement material would have negligible or no ODP, as well as an acceptable global warming potential (GWP).

1-Bromo-3,3,3-trifluoropropene, 2-bromo-3,3,3-trifluoropropene and 1,2-dibromo-3,3,3-trifluoropropene each have desirable ODP and GWP, and could potentially used as high efficiency fire extinguisher agents. For example, CN 102319498 A describes a dry powder fire extinguisher having 2-5 wt % of 2-bromo-3,3,3-trifluoropropene, the composition having high moisture-proof performance, high reburning resistance, and high fire extinguishing efficiency. Similarly, Zhang et al found a bromotrifluoropropene/zeolite mixture to be a highly efficient fire extinguisher (*Zhongguo Anquan Kexue Xuebao* 2011, 21(5), 53; *Process Safety and Environmental Protection* 2007, 85(B2), 147; *Huozai Kexue* (2010), 19(2), 60-67). 1-Bromo-3,3,3-trifluoropropene with an inert gas have many of the desirable properties of HALON 1301 fire extinguishing agents. The results show that the composites loaded with bromotrifluoropropene exhibited much better performance than that of common dry powders in putting out gasoline fires, requiring less powder, and having shorter fire extinguishing time.

One existing production process for 1-Bromo-3,3,3-trifluoropropene requires the reaction of 3,3,3-trifluoropropene with bromine, followed by dehydrobromination, to give the target compound. This process is very expensive, and not suitable for large quantity production.

Other production processes for bromotrifluoropropenes have been investigated. *J. Chem. Soc.* 1951, 2495 describes bromination of CF3CH=CH2 followed by alkaline treatment to give 2-bromo-3,3,3-trifluoropropene. *J. Chem. Soc.* 1952, 3490 describes hydrogen bromide (HBr) reaction with 3,3,3-trifluoropropyne at 0° C. or with AlBr$_3$ at −25° C. to give 1-bromo-3,3,3-trifluoropropene at high yield. Also, HBr reacted with 3,3,3-trifluoropropyne in a sealed cylinder with or without AlBr$_3$ yields 1-bromo-3,3,3-trifluoropropene in high yield (83-91% yield) when reacted at low temperatures (*J. Chem. Soc.* 1952, 3490; *J. Am. Chem. Soc.* 1952, 650). 2-Bromo-3,3,3-trifluoropropene is an important intermediate for pharmaceutical and agrochemicals and was often used as the precursor of 3,3,3-trifluoroacetylenic anion and could dehydrobrominated with LDA or BuLi at 0° C. (*J. Org. Chem.* 2009, 7559-61; *J. Flu. Chem.* 1996, 80, 145-7). Finally, Mori et al used 1,2-dibromo-3,3,3-trifluoropropene reacting with 20% aqueous NaOH to produce 2-bromo-3,3,3-trifluoropropene in 98% yield (JP 2001322955).

SUMMARY OF THE INVENTION

There remains a need for an improved process which may be used to efficiently produce bromotrifluoropropenes, and especially 1-bromo-3,3,3-trifluoropropene, in commercial quantities.

To this end, in accordance with one aspect of the present invention, a process of synthesizing bromotrifluoropropenes comprising mixing 3,3,3-trifluoropropyne with hydrogen bromide to make a first mixture, and subsequently contacting the first mixture with a catalyst at a temperature of at least 50° C. to yield at least one bromotrifluoropropene is provided.

Additionally, in accordance with a second aspect of the present invention, a process of synthesizing bromotrifluoropropenes comprising reacting 3,3,3-trifluoropropyne with hydrogen bromide without a catalyst at a temperature of at least 50° C. to yield at least one bromotrifluoropropene is provided.

DETAILED DESCRIPTION

In accordance with the present invention, it was found that 3,3,3-trifluoropropyne could react with HBr at high temperature under the influence of Lewis acid such as CuBr$_2$, CuBr, ZnBr$_2$, MgBr$_2$, AlBr$_3$, and other metal bromides (MBrx) to yield a product which contains a mixture of brominated olefins. Typically, the major product yielded was 1-bromo-3,3,3-trifluoropropene, but 2-bromo-3,3,3-trifluoropropene and 1,2-dibromo-3,3,3-trifluoropropene were also produced.

A variety of ionic solvents can be used for the reaction of 3,3,3-trifluoropropyne with HBr, for example, 1-alkyl-3-methylimidazolium, 1-alkylpyridinium, N-methyl-N-alkylpyrrolidinium and ammonium ions; however, an ionic solvent is not necessary. If an ionic solvent is used, 1-alkyl-3-methylimidazolium bromide is preferred, but a reaction having no such solvent is most preferred.

Catalysts can also be used. These include mineral acids such as H$_2$SO$_4$ or Lewis acids such as metal salts, especially those of copper, aluminum and antimony (e.g. CuBr$_2$, CuBr, and AlBr$_3$). Depending on the temperature of the reaction, the catalyst may not be necessary.

Reaction temperatures, for reactions at atmospheric pressure, were limited to 50-350° C., but the reaction might proceed at temperatures well above 350° C. To find the appropriate reaction temperature, a pre-mixed 3,3,3-trifluoropropyne and HBr was passed through the heated catalyst/solvent mixture and heating was continued until evidence of reaction was observed, for example, a measured release of heat or generation of volatiles.

Preferably, the molar ratio of HBr to 3,3,3-trifluoropropyne should be at least one, and can be higher; however, ratios in excess of 3 were not found to be particularly advantageous, and might increase the incidence of side reactions. Molar ratios in the range of 1.1 to 2.5 are particularly preferred.

In an example embodiment, HBr and 3,3,3-trifluoropropyne are mixed in a stainless cylinder and passed through a mixture of ionic liquid and catalyst or catalyst loaded on activated carbon at 50-350° C. Nitrogen or argon at a speed of 20 ml/m to 100 ml/m is used as a carrying gas. Reactants are controlled by a regulating valve at a rate of 10-50 ml/m. Product out of the reaction vessel is collected by a cooling trap at temperature of −20° C. to −78° C.

The following examples further illustrate the present invention, but should not be construed to limit the scope of the invention in any way.

EXAMPLES

Example 1

3.52 g of CuBr was dissolved in 18 ml of 48% HBr acid at 0° C. To this solution was added 31.7 g of activated carbon (Shirasagi granular, G2 X 4/b-1) under argon. The mixture was briefly vacuumed and then settled under argon overnight. The solvent was removed under vacuum (<80° C.), then heated at 100° C. for 2 hours.

Example 2

4.40 g of catalyst from Example 1 was heated in a 10 mm diameter Monel tube in the oven at 300° C. for 4 hours under nitrogen flow of 100 ml/m. Then, the oven was cooled to 250° C., nitrogen flow decreased to 20 ml/m, and 13.0 g of TFP and 15.0 g of HBr mixture in a cylinder was passed through the tube at 250° C. The product of 26.1 g clear liquid was collected in −78° C. trap. NMR analysis showed the presence of 9.47% Cis-1-bromo-3,3,3-trifluoropropene (−61.0 ppm, dd, J=7.6, 19.6 Hz), 64.79% trans-1-bromo-3,3,3-trifluoropropene (−64.7 ppm, dd, J=6.1, 20.1 Hz), 15.40% cis-1,2-dibromo-3,3,3-trifluoropropene (−66.5 ppm, d, J=19.8 Hz,), 10.33% 2-bromo-3,3,3-trifluoropropene (−69.4 ppm, d, J=19.6 Hz).

Example 3

The CuBr catalyst from Example 2 was reused. The oven was heated to 100° C., and 4.30 g of TFP and 8.10 g of HBr mixture in a cylinder was passed through the tube at 100° C. with nitrogen flow at 20 ml/m. The product of 5.2 g orange liquid was collected in a −78° C. trap. NMR and GC analysis showed that the liquid comprised 23.0% of 3,3,3-trifluoropropyne, 10.60% of cis-1-bromo-3,3,3-trifluoropropene, 56.77% of trans-1-bromo-3,3,3-trifluoropropene, 1.13% of 1,2-dibromo-3,3,3-trifluoropropene, 3.24% of 2-bromo-3,3,3-trifluoropropene, as well as some unidentified products.

What is claimed is:

1. A process of synthesizing bromotrifluoropropenes, the process comprising the steps of:
    mixing 3,3,3-trifluoropropyne with hydrogen bromide to make a first mixture; and,
    contacting the first mixture with a catalyst at a temperature of at least 50° C. to yield at least one bromotrifluoropropene.
2. The process of claim 1, wherein the at least one trifluoropropene comprises trans-1-bromo-3,3,3-trifluoropropene.
3. The process of claim 1, wherein the at least one trifluoropropene comprises cis-1-bromo-3,3,3-trifluoropropene.
4. The process of claim 1, wherein the at least one trifluoropropene comprises 2-bromo-3,3,3-trifluoropropene.
5. The process of claim 1, wherein the contacting step is conducted in the absence of an ionic solvent.
6. The process of claim 1, wherein the contacting step is conducted in the presence of an ionic solvent.
7. The process of claim 6, wherein the ionic solvent is selected from the group consisting of 1-alkyl-3-methylimidazolium, 1-alkylpyridinium, N-methyl-N-alkylpyrrolidinium and ammonium ions.
8. The process of claim 6, wherein the ionic solvent comprises 1-alkyl-3-methylimidazolium bromide.
9. The process of claim 1, wherein the catalyst is selected from the group consisting of mineral acids and Lewis acids.
10. The process of claim 9, wherein the catalyst is a metal salt.
11. The process of claim 10, wherein the metal salt comprises copper, aluminum or antimony.
12. The process of claim 1, wherein the contacting step is conducted at a temperature of between 50 and 350° C.
13. The process of claim 1, wherein the molar ratio of HBr to 3,3,3-trifluoropropyne is at least 1 in the first mixture.
14. The process of claim 13, wherein the molar ratio of HBr to 3,3,3-trifluoropropyne is in the range of 1.1 to 2.5.
15. A process of synthesizing bromotrifluoropropenes, the process comprising reacting 3,3,3-trifluoropropyne with hydrogen bromide without a catalyst at a temperature of at least 50° C. to yield at least one bromotrifluoropropene.

* * * * *